(12) United States Patent
Williams (10) Patent No.: US 11,331,310 B2
(45) Date of Patent: May 17, 2022

(54) METHOD OF TREATING COCAINE ADDICTION

(71) Applicant: MyMD Pharmaceuticals (Florida), Inc., Tampa, FL (US)

(72) Inventor: Jonnie R. Williams, Sarasota, FL (US)

(73) Assignee: MyMD Pharmaceuticals (Florida), Inc., Tampa, FL (US)

( * ) Notice: Subject to any disclaimer, the term of this patent is extended or adjusted under 35 U.S.C. 154(b) by 299 days.

(21) Appl. No.: 16/679,379

(22) Filed: Nov. 11, 2019

(65) Prior Publication Data

US 2020/0215045 A1 Jul. 9, 2020

Related U.S. Application Data

(63) Continuation of application No. 15/875,692, filed on Jan. 19, 2018, now Pat. No. 10,471,052, which is a continuation-in-part of application No. 15/670,012, filed on Aug. 7, 2017, now Pat. No. 9,884,055, which is a continuation-in-part of application No. PCT/US2016/018047, filed on Feb. 16, 2016.

(60) Provisional application No. 62/118,136, filed on Feb. 19, 2015.

(51) Int. Cl.
  *A61K 31/4439* (2006.01)
  *A61K 45/06* (2006.01)
  *A61P 25/36* (2006.01)
  *A61P 25/32* (2006.01)
  *A61P 25/30* (2006.01)

(52) U.S. Cl.
  CPC .......... *A61K 31/4439* (2013.01); *A61K 45/06* (2013.01); *A61P 25/30* (2018.01); *A61P 25/32* (2018.01); *A61P 25/36* (2018.01)

(58) Field of Classification Search
  None
  See application file for complete search history.

(56) References Cited

U.S. PATENT DOCUMENTS

| | | |
|---|---|---|
| 5,276,043 A | 1/1994 | Lippiello et al. |
| 6,041,789 A | 3/2000 | Bankert et al. |
| 6,350,479 B1 | 2/2002 | Williams et al. |
| 6,552,035 B2 | 4/2003 | Park et al. |
| 7,726,320 B2 | 6/2010 | Robinson et al. |
| 7,832,410 B2 | 11/2010 | Hon |
| 2002/0025300 A1 | 2/2002 | Wolfson et al. |

(Continued)

FOREIGN PATENT DOCUMENTS

WO 2009105919 A1 9/2009

OTHER PUBLICATIONS

Gupta et al., Indian J Psychiatry. Apr.-Jun. 2007; 49(2): 85-90 (Year: 2007).*

(Continued)

*Primary Examiner* — Karl J Puttlitz
(74) *Attorney, Agent, or Firm* — Banner & Witcoff, Ltd.

(57) ABSTRACT

A pharmaceutical composition containing isomyosmine or a pharmaceutically acceptable salt thereof is administered to an individual in need thereof for treating a substance addiction, inclusive of addiction to heroin (diacetylmorphine), cocaine, opioids, methadone, d-methamphetamine, barbiturates, alcohol, benzodiazepines, amphetamines, or buprenorphine. The isomyosmine, along with optional additional therapeutic agent(s), may be administered in a capsule, tablet, or lozenge.

10 Claims, 2 Drawing Sheets

(56) References Cited

U.S. PATENT DOCUMENTS

| | | |
|---|---|---|
| 2002/0054926 A1 | 5/2002 | Williams et al. |
| 2004/0013752 A1 | 1/2004 | Wolfson |
| 2005/0172976 A1 | 8/2005 | Newman et al. |
| 2005/0260420 A1 | 11/2005 | Collins et al. |
| 2007/0267031 A1 | 11/2007 | Hon |
| 2008/0156336 A1 | 7/2008 | Wyss-Peters et al. |
| 2008/0188527 A1 | 8/2008 | Cashman |
| 2008/0241255 A1 | 10/2008 | Rose et al. |
| 2008/0257367 A1 | 10/2008 | Paterno et al. |
| 2009/0126745 A1 | 5/2009 | Hon |
| 2009/0272379 A1 | 11/2009 | Thorens et al. |
| 2010/0160376 A1 | 6/2010 | Thompson |
| 2010/0236562 A1 | 9/2010 | Hearn et al. |
| 2011/0005535 A1 | 1/2011 | Xiu |
| 2011/0237627 A1 | 9/2011 | Puthiaparampil et al. |
| 2011/0265806 A1 | 11/2011 | Alarcon et al. |
| 2012/0003341 A1 | 1/2012 | Williams et al. |
| 2012/0186594 A1 | 7/2012 | Liu |
| 2012/0325228 A1 | 12/2012 | Williams |
| 2014/0345635 A1 | 11/2014 | Rabinowitz et al. |

OTHER PUBLICATIONS

D.K. Hatsukami et al., Nicotine reduction revisited: science and future directions, Tobacco Control 19: e1-e10 (2010).

J.S. Fowler et al., Inhibition of Monoamine Oxidase B in the Brain of Smokers, Nature (Lond), 379(6567):733 736 (1996).

J. Stephenson, Clues Found to Tobacco Addiction, Journal of the American Medical Association, 275(16): 1217-1218 (1996).

P. H. Stahl et al., Handbook of Pharmaceutical Salts: Properties, Selection and Use, Weinheim/Wiley-VCH/VHCA, 2002, pp. 269-310.

Receptors for Nicotine in the Central Nervous System: 1 Radioligand Binding Studies, Group Research & Development Centre, British-American Tobacco Co. Ltd. (1984).

DVapon, "Whole Tobacco Alkaloid E-liquid," Nov. 26, 2009, http://www.e-cigarette-forum.com/forum/blogs/dvap/423-whole-tobacco-alkaloid-e-liquid.html.

Westenberger, B.J., Deputy Director, "Evaluation of e-cigarettes," FDA memorandum dated May 4, 2009, DPATR-FY-09-23, 8 pages.

Jan. 7, 2013—(PCT) International Search Report—App No. PCT/US2012/042710.

Gupta et al., Indian J. Psychiatry. Apr.-Jun. 2007; 49(2): 85-90.

Yang, Hai-Yu; Wu, Zhi-Yuan; Wood, Mark; Whiteman, Matthew; and Bian, Jin-Song, Hydrogen Sulfide Attenuates Opioid Dependence by Suppression of Adenylate Cyclase/cAMP Pathway, Antioxidants & Redox Signaling, vol. 20, No. 1, (2014) pp. 31-41.

MyMD Pharmaceuticals, Inc., Clinical Hold Complete Response, Submitted to the Food & Drug Administration on Sep. 14, 2021, 17 pages.

\* cited by examiner

METHOD OF TREATING COCAINE ADDICTION

CROSS REFERENCE TO RELATED APPLICATIONS

This application is a continuation of U.S. application Ser. No. 15/875,692, filed Jan. 19, 2018, now U.S. Pat. No. 10,471,052, which is a continuation-in-part of U.S. application Ser. No. 15/670,012, filed Aug. 7, 2017, now U.S. Pat. No. 9,884,055, which is a continuation-in-part of International Application PCT/US2016/018047, filed Feb. 16, 2016, which claims priority under 35 U.S.C. § 119(e) to U.S. Provisional Application No. 62/118,136, filed Feb. 19, 2015, the disclosures of which are hereby incorporated by reference in their entireties.

BACKGROUND

Monoamine oxidase (MAO) inhibitors can regulate the level of monoamines and their neurotransmitter release in different brain regions and in the body (including dopamine, norepinephrine, and serotonin). MAO inhibitors (MAOI) can thereby affect the modulation of neuroendocrine function, respiration, mood, motor control and function, focus and attention, concentration, memory and cognition, and the mechanisms of substance abuse. MAOI have been demonstrated to have effects on attention, cognition, appetite, substance abuse, memory, cardiovascular function, extrapyramidal function, pain and gastrointestinal motility and function. The distribution of MAO in the brain is widespread and includes the basal ganglia, cerebral cortex, limbic system, and mid and hind brain nuclei. In the peripheral tissue, the distribution includes muscle, the gastrointestinal tract, the cardiovascular system, autonomic ganglia, the liver, and the endocrinic system. Regulation of monoamine levels in the body has been shown to be effective in numerous disease states including depression, anxiety, stress disorders, and withdrawal symptoms, among others.

It has been suggested that cigarette smoke may have irreversible inhibitory effect towards monoamine oxidase (MAO). A. A. Boulton et al., "Biogenic Amine Adducts, Monoamine Oxidase Inhibitors, and Smoking," Lancet, 1 (8577):114-155 (1988), reported that the MAO inhibiting properties of cigarette smoke may help to explain the protective action of smoking against Parkinson's disease and also observed that patients with mental disorders who smoke heavily do not experience unusual rates of smoking induced disorders. It was suggested that smoking, as an MAOI, may protect against dopaminergic neurotoxicity that leads to Parkinson's disease and that the MAO inhibiting properties of smoking may result in an anti-depressive effect in mental patients.

L. A. Carr et al., "Effects of Tobacco Smoke Constituents on MPTP-Induced Toxicity and Monoamine Oxidase Activity in the Mouse Brain," Life Sciences, 48:1173 1177 (1991), found that nicotine, 4-phenylpyridine and hydrazine prevented the decrease in dopamine metabolite levels induced by 1-methyl-4-phenyl-1,2,3,6-tetrahydropyridine (MPTP) in mice, but there was no significant effect on dopamine levels. Because tobacco smoke particulate matter caused a marked inhibition of MAO-A and MAO-B activity when added in vitro, it was suggested that one or more unidentified substances in tobacco smoke are capable of inhibiting brain MAO and perhaps altering the formation of the active metabolite of MPTP.

J. S. Fowler et al., "Inhibition of Monoamine Oxidase B in the Brain of Smokers," Nature (Lond), 379(6567): 733 736 (1996), found that the brains of living smokers showed a 40% decrease in the level of MAO-B relative to nonsmokers or former smokers. MAO inhibition was also reported as being associated with decreased production of hydrogen peroxide.

It has also been suggested that nicotine may not be the only constituent of tobacco responsible for tobacco addiction. J. Stephenson, "Clues Found to Tobacco Addiction," Journal of the American Medical Association, 275(16): 1217 1218 (1996), discussing the work of Fowler, et al., pointed out that the brains of living smokers had less MAO-B compared with the brains of nonsmokers or former smokers. MAO-B is an enzyme involved in the breakdown of dopamine, which is a pleasure-enhancing neurotransmitter. The results suggested that the inhibition of MAO-B in the brains of smokers may make nicotine more addictive by slowing down the breakdown of dopamine, thereby boosting its levels. The findings provided an explanation as to why cigarette smokers were less susceptible to developing Parkinson's disease. Further, the findings suggested that MAOI could be used for smoking cessation. Williams et al. U.S. Pat. No. 6,350,479 reported that the minor tobacco alkaloids anabasine, anatabine, and nornicotine exhibited MAO inhibitory effects against MAO-A and MAO-B.

There remains a need for alternative therapies for treating substance addictions and for assisting individuals in reducing or eliminating cravings for nicotine or dependence on nicotine.

SUMMARY

In accordance with aspects disclosed herein, compositions containing isomyosmine or a pharmaceutically acceptable salt thereof may be administered to an individual in need thereof for treating substance addiction, such as tobacco- or other substance addiction, including smoking addiction, smokeless tobacco addiction, and other forms of nicotine dependence. A substance addiction may be, example, an addiction to heroin (diacetylmorphine), cocaine, opioids, methadone, d-methamphetamine, barbiturates, alcohol, benzodiazepines, amphetamines, or buprenorphine. In some examples, isomyosmine or a pharmaceutically acceptable salt thereof is administered, with or without other active agent(s), in a capsule, tablet, or lozenge. In other examples, isomyosmine or a pharmaceutically acceptable salt thereof is administered, with or without other active agent(s), via a chewing gum, inhalation spray, e-cigarette, or transdermal patch.

The present inventor found that isomyosmine is a potent inhibitor of monoamine oxidase (MAO), including both MAO-A and MAO-B. Through these and/or other mechanisms (e.g., anti-inflammatory properties), isomyosmine may be particularly effective for treating substance addiction, inclusive of affecting smoking substitution and/or assisting individuals in reducing or eliminating cravings for nicotine or dependence on nicotine.

BRIEF DESCRIPTION OF THE DRAWINGS

A more complete understanding of the present invention and certain advantages thereof may be acquired by referring to the following detailed description in consideration with the accompanying drawings, in which.

DETAILED DESCRIPTION

Aspects of the present specification disclose, in part, a pharmaceutical composition. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as any of the therapeutic compounds disclosed herein. A pharmaceutical composition may be administered to an individual alone, or in combination with other supplementary active ingredients, agents, drugs or hormones.

A pharmaceutical composition disclosed herein may include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle," "stabilizer," "diluent," "additive," "auxiliary" or "excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

Unless otherwise clear from context, all percentages referred to herein are expressed as percent by weight based on the total weight of the composition. Percentages expressed herein as "w/v" refer to mass, in grams, of the component per 100 ml of solvent. For example, a 1% (w/v) composition of isomyosmine contains 1 g (1000 mg) of isomyosmine per 100 ml of solvent, which is equivalent to 10 mg/ml.

Isomyosmine (3-(3,4-dihydro-2H-pyrrol-2-yl)-pyridine) is a nicotine related alkaloid present in solanecea plants containing nicotine.

Isomyosmine may be prepared synthetically using known techniques, and also is commercially available from several chemical suppliers. Isomyosmine has two optical isomers (+/−) owing to an asymmetric carbon atom within its pyrrole ring that joins to the pyridine ring. Unless otherwise clear from context, the term "isomyosmine," as used herein, is inclusive of enantiomeric mixtures (+/−) including racemic mixtures, as well as isolated forms of one or the other enantiomer.

In some embodiments, isomyosmine may be adsorbed on a cation exchange resin such as polymethacrilic acid (Amberlite IRP64 or Purolite C115HMR), as described in U.S. Pat. No. 3,901,248, the disclosure of which is hereby incorporated by reference in its entirety. Such cation exchange resins have been used commercially, for example, in nicotine replacement therapy, e.g., nicotine polacrilex.

Unless otherwise clear from context, "isomyosmine" as used herein refers to both salt and non-salt forms of isomyosmine. Non-limiting examples of possible salts are described in P. H. Stahl et al., Handbook of Pharmaceutical Salts: Properties, Selection and Use, Weinheim/Zürich:Wiley-VCHNHCA, 2002, including salts of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid.

As an alternative to synthetic preparation, isomyosmine may be obtained by extraction from tobacco or other materials in which it occurs naturally. For example, tobacco material may extracted with a solvent, such as water, ethanol, steam, and/or carbon dioxide. The resulting solution contains the soluble components of the tobacco, including alkaloids such as nicotine, isomyosmine, and myosmine. Isomyosmine (as well as other extracted components, such as nicotine, if desired) may be purified using known techniques such as liquid chromatography. Nicotine and/or other alkaloid components, when used, likewise may be prepared synthetically or extracted from appropriate natural materials.

In pharmaceutical applications, an isolated form of isomyosmine generally is used. An "isolated form of isomyosmine," as used herein, refers to isomyosmine that either has been prepared synthetically or has been substantially separated from natural materials in which it occurs. The isolated form of isomyosmine should have a very high purity (including enantiomeric purity in the case where an enantiomer is used). In the case of synthetic isomyosmine, for example, purity refers to the ratio of the weight of isomyosmine to the weight of the end reaction product. In the case of isolating isomyosmine from native material, for example, purity refers to the ratio of the weight of isomyosmine to the total weight of the isomyosmine-containing extract. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Compositions may contain isomyosmine, alone or with other therapeutic compound(s). A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g., a hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. In some aspects, the therapeutic compound may have anti-inflammatory activity, such as a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, aceclofenac, acemetacin, actarit, alcofenac, alminoprofen, amfenac, aloxipirin, aminophenazone, antraphenine, aspirin, azapropazone, benorilate, benoxaprofen, benzydamine, butibufen, celecoxib, chlorthenoxacin, choline salicylate, clometacin, dexketoprofen, diclofenac, diflunisal, emorfazone, epirizole; etodolac, etoricoxib, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, lumiracoxib, mefenamic acid, meloxicam, metamizole, metiazinic acid, mofebutazone, mofezolac, nabumetone, naproxen, nifenazone, niflumic acid, oxametacin, phenacetin, pipebuzone, pranoprofen, propyphenazone, proquazone, protizinic acid, rofecoxib, salicylamide, salsalate, sulindac, suprofen, tiaramide, tinoridine, tolfenamic acid, valdecoxib, and zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase-1 (COX-1) inhibitor, and a selective cyclooxygenase-2 (COX-2) inhibitor. An NSAID may be a profen. Examples of a suitable salicylate derivative NSAID include, without limitation, acetylsalicylic acid (aspirin), diflunisal, and salsalate. Examples of a suitable p-amino phenol derivative NSAID include, without limitation, paracetamol and phenacetin. Examples of a suitable propionic acid derivative NSAID include, without limitation, alminoprofen, benoxaprofen, dexketoprofen, fenoprofen, flurbiprofen, ibuprofen, indoprofen, ketoprofen, loxoprofen, naproxen, oxaprozin, pranoprofen, and suprofen. Examples of a suitable acetic acid derivative NSAID include, without limitation, aceclofenac, acemetacin, actarit, alcofenac, amfenac, clometacin, diclofenac, etodolac, felbinac, fenclofenac, indometacin, ketorolac, metiazinic acid, mofezolac, nabumetone, naproxen, oxametacin, sulindac, and zomepirac. Examples of a suitable enolic acid (oxicam) derivative NSAID include, without limitation, droxicam, isoxicam, lornoxicam, meloxicam, piroxicam, and tenoxicam. Examples of a suitable fenamic acid derivative NSAID include, without limitation, flufenamic acid, mefenamic acid, meclofenamic acid, and tolfenamic acid. Examples of a suitable selective COX-2 inhibitors include, without limitation, celecoxib, etoricoxib, firocoxib, lumiracoxib, meloxicam, parecoxib, rofecoxib, and valdecoxib.

Isomyosmine may be administered for treating tobacco or other substance addiction, including promoting smoking cessation or otherwise assisting individuals in reducing or eliminating cravings for nicotine or dependence on nicotine. Isomyosmine was found to be a potent inhibitor of monoamine oxidase (MAO), including both MAO-A and MAO- B. Through these and/or other mechanisms, pharmaceutical compositions containing isomyosmine may be particularly effective for treating tobacco addiction and/or for assisting individuals in reducing or eliminating cravings for nicotine or dependence on nicotine.

A therapeutic compound disclosed herein may be an ester of a therapeutic compound. In general, an ester of a therapeutic compound increases the log P value relative to the same therapeutic compound without the ester modification. An ester group may be attached to a therapeutic compound by, e.g., a carboxylic acid or hydroxyl functional group present of the therapeutic compound. An ester of a therapeutic compound may have an increased hydrophobicity, and as such, may be dissolved in a reduced volume of solvent disclosed herein. In some instances, an ester of a therapeutic compound may be combined directly with an adjuvant disclosed herein, thereby eliminating the need of a solvent. An ester of a therapeutic compound may enable the making of a pharmaceutical composition disclosed herein, in situations where a non-esterified form of the same therapeutic compound is otherwise immiscible in a solvent disclosed herein. An ester of a therapeutic compound may still be delivered in a manner that more effectively inhibits a pro-inflammatory response as long as the compound is combined with an adjuvant disclosed herein. In one embodiment, a therapeutic compound may be reacted with ethyl ester in order to form an ethyl ester of the therapeutic compound.

A pharmaceutical composition may comprise a therapeutic compound in an amount sufficient to allow customary administration to an individual. In aspects of this embodiment, a pharmaceutical composition disclosed herein may be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

Pharmaceutical compositions as described herein may include a pharmaceutically acceptable solvent. A solvent is a liquid, solid, or gas that dissolves another solid, liquid, or gaseous (the solute), resulting in a solution. Solvents useful in the pharmaceutical compositions include, without limitation, a pharmaceutically acceptable polar aprotic solvent, a pharmaceutically acceptable polar protic solvent and a pharmaceutically acceptable non-polar solvent. A pharmaceutically acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically acceptable non-polar solvent includes, without limitation, pentane, cyclopentane, hexane, cyclohexane, benzene, toluene, 1,4-dioxane, chloroform, n-methyl-pyrrilidone (NMP), and diethyl ether.

A pharmaceutical composition disclosed herein may comprise a solvent in an amount sufficient to dissolve a therapeutic compound disclosed herein. In other aspects of this embodiment, a pharmaceutical composition disclosed herein may comprise a solvent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

In one embodiment, a solvent may comprise a pharmaceutically acceptable alcohol. As used herein, the term "alcohol" refers to an organic molecule comprising a hydroxyl functional group (—OH) bonded to a carbon atom, where the carbon atom is saturated. In aspects of this embodiment, the alcohol may be, e.g., a C1-4 alcohol, a C2-4 alcohol, a C1-5 alcohol, a C1-7 alcohol, a C1-10 alcohol, a C1-15 alcohol, or a C1-20 alcohol. In other aspects of this embodiment, an alcohol may be, e.g., a primary alcohol, a secondary alcohol, or a tertiary alcohol. In other aspects of this embodiment, an alcohol may be, e.g., an acyclic alcohol, a monohydric alcohol, a polyhydric alcohol (also known as a polyol or sugar alcohol), an unsaturated aliphatic alcohol, an alicyclic alcohol, or a combination thereof. Examples of a monohydric alcohol include, without limitation, methanol, ethanol, propanol, butanol, pentanol, and 1-hexadecanol. Examples of a polyhydric alcohol include, without limitation, glycol, glycerol, arabitol, erythritol, xylitol, maltitol, sorbitol (gluctiol), mannitol, inositol, lactitol, galactitol (iditol), and isomalt. Examples of an unsaturated aliphatic alcohol include, without limitation, prop-2-ene-1-ol, 3,7-dimethylocta-2,6-dien-1-ol, and prop-2-in-1-ol. Examples of an alicyclic alcohol include, without limitation, cyclohexane-1,2,3,4,5,6-hexyl and 2-(2-propyl)-5-methyl-cyclohexane-1-ol.

In another embodiment, a solvent may comprise an ester of pharmaceutically acceptable alcohol and an acid. Suitable pharmaceutically acceptable alcohols include the ones disclosed herein. Suitable acids include, without limitation, acetic acid, butaric acid, and formic acid. An ester of an alcohol and an acid include, without limitation, methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate.

In another embodiment, a solvent may comprise a pharmaceutically acceptable polyethylene glycol (PEG) polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a solvent may comprise a pharmaceutically acceptable glyceride. Glycerides comprise a substituted glycerol, where one, two, or all three hydroxyl groups of the glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides.

In one embodiment, a solvent may comprise a pharmaceutically acceptable solid solvent. Solid solvents may be useful in the manufacture of a solid dose formulation of a pharmaceutical composition disclosed herein. Typically, a solid solvent is melted in order to dissolve a therapeutic compound. A pharmaceutically acceptable solid solvent includes, without limitation, menthol and PEG polymers described above.

Aspects of the present specification disclose, in part, a pharmaceutically acceptable adjuvant. An adjuvant is a pharmacological agent that modifies the effect of other agents, such as one or more therapeutic compounds disclosed herein. In addition, an adjuvant disclosed herein may be used as a solvent that dissolves a therapeutic compound disclosed herein, forming an adjuvant solution. An adjuvant may facilitate delivery of a therapeutic compound in a manner that more effectively inhibits a pro-inflammatory response. In one embodiment, an adjuvant facilitates the delivery of a therapeutic compound into macrophages.

A pharmaceutical composition may comprise a pharmaceutically acceptable adjuvant in an amount sufficient to mix with a solution or an emulsion. In other aspects of this embodiment, a pharmaceutical composition may comprise an adjuvant in an amount of, e.g., at least 10% (v/v), at least 20% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v), at least 80% (v/v), at least 85% (v/v), at least 90% (v/v), at least 95% (v/v), or at least 99% (v/v). In other aspects of this embodiment, a pharmaceutical composition may comprise an adjuvant in an amount in a range of, e.g., about 30% (v/v) to about 99% (v/v), about 35% (v/v) to about 99% (v/v), about 40% (v/v) to about 99% (v/v), about 45% (v/v) to about 99% (v/v), about 50% (v/v) to about 99% (v/v), about 30% (v/v) to about 98% (v/v), about 35% (v/v) to about 98% (v/v), about 40% (v/v) to about 98% (v/v), about 45% (v/v) to about 98% (v/v), about 50% (v/v) to about 98% (v/v), about 30% (v/v) to about 95% (v/v), about 35% (v/v) to about 95% (v/v), about 40% (v/v) to about 95% (v/v), about 45% (v/v) to about 95% (v/v), or about 50% (v/v) to about 95% (v/v). In yet other aspects of this embodiment, a pharmaceutical composition may comprise an adjuvant in an amount in a range of, e.g., about 70% (v/v) to about 97% (v/v), about 75% (v/v) to about 97% (v/v), about 80% (v/v) to about 97% (v/v), about 85% (v/v) to about 97% (v/v), about 88% (v/v) to about 97% (v/v), about 89% (v/v) to about 97% (v/v), about 90% (v/v) to about 97% (v/v), about 75% (v/v) to about 96% (v/v), about 80% (v/v) to about 96% (v/v), about 85% (v/v) to about 96% (v/v), about 88% (v/v) to about 96% (v/v), about 89% (v/v) to about 96% (v/v), about 90% (v/v) to about 96% (v/v), about 75% (v/v) to about 93% (v/v), about 80% (v/v) to about 93% (v/v), about 85% (v/v) to about 93% (v/v), about 88% (v/v) to about 93% (v/v), about 89% (v/v) to about 93% (v/v), or about 90% (v/v) to about 93% (v/v).

In one embodiment, an adjuvant may be a pharmaceutically acceptable lipid. A lipid may be broadly defined as a hydrophobic or amphiphilic small molecule. The amphiphilic nature of some lipids allows them to form structures such as vesicles, liposomes, or membranes in an aqueous environment. Non-limiting examples, of lipids include fatty acids, glycerolipids (like monoglycerides, diglycerides, and triglycerides), phospholipids, sphingolipids, sterol lipids, prenol lipids, saccharolipids, and polyketides. A pharmaceutical composition disclosed herein may comprise a lipid such as, e.g. an oil, an oil-based liquid, a fat, a fatty acid, a wax, a fatty acid ester, a fatty acid salt, a fatty alcohol, a glyceride (mono-, di- or tri-glyceride), a phospholipids, a glycol ester, a sucrose ester, a glycerol oleate derivative, a medium chain triglyceride, or a mixture thereof.

A lipid useful in the pharmaceutical compositions may be a pharmaceutically acceptable fatty acid. A fatty acid comprises a carboxylic acid with a long unbranched hydrocarbon chain which may be either saturated or unsaturated. Thus arrangement confers a fatty acid with a polar, hydrophilic end, and a nonpolar, hydrophobic end that is insoluble in water. Most naturally occurring fatty acids have a hydrocarbon chain of an even number of carbon atoms, typically between 4 and 24 carbons, and may be attached to functional groups containing oxygen, halogens, nitrogen, and sulfur. Synthetic or non-natural fatty acids may have a hydrocarbon chain of any number of carbon atoms from between 3 and 40 carbons. Where a double bond exists, there is the possibility of either a cis or a trans geometric isomerism, which significantly affects the molecule's molecular configuration. Cis-double bonds cause the fatty acid chain to bend, an effect that is more pronounced the more double bonds there are in a chain. Most naturally occurring fatty acids are of the cis configuration, although the trans form does exist in some natural and partially hydrogenated fats and oils. Examples of fatty acids include, without limitation, capryllic acid (8:0), pelargonic acid (9:0), capric acid (10:0), undecylic acid (11:0), lauric acid (12:0), tridecylic acid (13:0), myristic acid (14:0), myristoleic acid (14:1), pentadecyclic acid (15:0), palmitic acid (16:0), palmitoleic acid (16:1), sapienic acid (16:1), margaric acid (17:0), stearic acid (18:0), oleic acid (18:1), elaidic acid (18:1), vaccenic acid (18:1), linoleic acid (18:2), linoelaidic acid (18:2), α-linolenic acid (18:3), γ-linolenic acid (18:3), stearidonic acid (18:4), nonadecylic acid (19:0), arachidic acid (20:0), eicosenoic acid (20:1), dihomo-γ-linolenic acid (20:3), mead acid (20:3), arachidonic acid (20:4), eicosapentaenoic acid (20:5), heneicosylic acid (21:0), behenic acid (22:0), erucic acid (22:1), docosahexaenoic acid (22:6), tricosylic acid (23:0), lignoceric acid (24:0), nervonic acid (24:1), pentacosylic acid (25:0), cerotic acid (26:0), heptacosylic acid (27:0), montanic acid (28:0), nonacosylic acid (29:0), melissic acid (30:0), henatriacontylic acid (31:0), lacceroic acid (32:0), psyllic acid (33:0), geddic acid (34:0), ceroplastic acid (35:0), and hexatriacontylic acid (36:0).

An adjuvant may be a pharmaceutically acceptable saturated or unsaturated fatty acid. A saturated or unsaturated fatty acid may comprise, e.g., at least 8, at least 10, at least 12, at least 14, at least 16, at least 18, at least 20, at least 22, at least 24, at least 26, at least 28, or at least 30 carbon atoms. In some instances, a saturated or unsaturated fatty acid comprises, e.g., between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms. If unsaturated, the fatty acid may have, e.g., 1 or more, 2 or more, 3 or more, 4 or more, 5 or more, or 6 or more double bonds.

A pharmaceutically acceptable saturated or unsaturated fatty acid may be liquid at room temperature. The melting point of a fatty acid is largely determined by the degree of saturation/unsaturation of the hydrocarbon chain. In aspects of this embodiment, a saturated or unsaturated fatty acid has a melting point temperature of, e.g., 20° C. or below, 15° C. or below, 10° C. or below, 5° C. or below, 0° C. or below, −5° C. or below, −10° C. or below, −15° C. or below, or −20° C. or below. In other aspects of this embodiment, a saturated or unsaturated fatty acid has a melting point temperature in the range of, e.g., about −20° C. to about 20° C., about −20° C. to about 18° C., about −20° C. to about 16° C., about −20° C. to about 12° C., about −20° C. to about 8° C., about −20° C. to about 4° C., about −20° C. to about 0° C., about −15° C. to about 20° C., about −15° C. to about 18° C., about −15° C. to about 16° C., about −15° C. to about 12° C., about −15° C. to about 8° C., about −15° C. to about 4° C., or about −15° C. to about 0° C.

An adjuvant may comprise one kind of pharmaceutically acceptable fatty acid. An adjuvant may comprise, for example, only palmitic acid, only stearic acid, only oleic acid, only linoleic acid, or only linolenic acid. Alternatively, an adjuvant may comprise a plurality of different pharmaceutically acceptable fatty acids. An adjuvant may comprise, e.g., two or more different fatty acids, three or more different fatty acids, four or more different fatty acids, five or more different fatty acids, or six or more different fatty acids.

An adjuvant may comprise two or more different pharmaceutically acceptable fatty acids including at least palmitic acid, stearic acid, oleic acid, linoleic acid and/or linolenic acid, and any combination thereof. An adjuvant may comprise a ratio of palmitic acid and/or stearic acid and/or oleic acid:linolenic acid and/or linoleic acid of, e.g., at least 2:1, at least 3:1, at least 4:1, at least 5:1, at least 6:1, at least 7:1, at least 8:1, at least 9:1, at least 10:1, at least 15:1, or at least 20:1. In some examples, an adjuvant may comprise a ratio of palmitic acid and/or stearic acid and/or oleic acid:linolenic acid and/or linoleic acid in a range of, e.g., about 1:1 to about 20:1, about 2:1 to about 15:1, about 4:1 to about 12:1, or about 6:1 to about 10:1.

An adjuvant may comprise four or more different pharmaceutically acceptable fatty acids including at least palmitic acid, stearic acid, oleic acid, linoleic acid and/or linolenic acid, and any combination thereof. In other aspects of this embodiment, an adjuvant may comprise a ratio of palmitic acid:stearic acid:linolenic acid:linoleic acid of, e.g., 10:10:1:1, 9:9:1:1, 8:8:1:1, 7:7:1:1, 6:6:1:1, 5:5:1:1, 4:4:1:1, 3:3:1:1, 2:2:1:1, or 1:1:1:1. In other aspects of this embodiment, an adjuvant may comprise a ratio of palmitic acid:stearic acid:linolenic acid:linoleic acid in a range of, e.g., about 10:10:1:1 to about 6:6:1:1, about 8:8:1:1 to about 4:4:1:1, or about 5:5:1:1 to about 1:1:1:1.

A lipid useful in the pharmaceutical compositions may be a pharmaceutically acceptable omega fatty acid. Non-limiting examples of an omega fatty acid include omega-3, omega-6, and omega-9. Omega-3 fatty acids (also known as n-3 fatty acids or ω-3 fatty acids) are a family of essential unsaturated fatty acids that have in common a final carbon-carbon double bond in the n-3 position, that is, the third bond, counting from the methyl end of the fatty acid. The omega-3 fatty acids are "essential" fatty acids because they are vital for normal metabolism and cannot be synthesized by the human body. An omega-3 fatty acid includes, without limitation, hexadecatrienoic acid (16:3), α-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), clupanodonic acid (22:5), docosahexaenoic acid (22:6), tetracosapentaenoic acid (24:5), and tetracosahexaenoic acid (nisinic acid) (24:6).

Omega-6 fatty acids (also known as n-6 fatty acids or ω-6 fatty acids) are a family of unsaturated fatty acids that have in common a final carbon-carbon double bond in the n-6 position, that is, the sixth bond, counting from the methyl end of the fatty acid. An omega-6 fatty acid includes, without limitation, linoleic acid (18:2), gamma-linolenic acid (18:3), calendic acid (18:3), eicosadienoic acid (20:2), dihomo-gamma-linolenic acid (20:3), arachidonic acid (20:4), docosadienoic acid (22:2), adrenic acid (22:4), docosapentaenoic acid (22:5), tetracosatetraenoic acid (24:4), and tetracosapentaenoic acid (24:5). Omega-9 fatty acids (also known as n-9 fatty acids or ω-9 fatty acids) are a family of unsaturated fatty acids that have in common a final carbon-carbon double bond in the n-9 position, that is, the ninth bond, counting from the methyl end of the fatty acid. An omega-9 fatty acid includes, without limitation, oleic acid (18:1), elaidic acid (18:1), eicosenoic acid (20:1), mead acid (20:3), erucic acid (22:1), and nervonic acid (24:1).

A lipid useful in the pharmaceutical compositions disclosed herein may be a pharmaceutically acceptable oil. An oil includes any fatty acid that is liquid at normal room temperature, such as, e.g. about 20° C. In contrast, a fat includes any fatty acid that is solid at normal room temperature, such as, e.g. about 20° C. An oil suitable as a lipid useful in the pharmaceutical compositions disclosed herein, may be a natural oil or a vegetable oil. Examples of suitable natural oils include, without limitation, mineral oil, triacetin, ethyl oleate, a hydrogenated natural oil, or a mixture thereof. Examples of suitable vegetable oils include, without limitation, almond oil, arachis oil, avocado oil, canola oil, castor oil, coconut oil, corn oil, cottonseed oil, grape seed oil, hazelnut oil, hemp oil, linseed oil (flax seed oil), olive oil, palm oil, peanut oil, rapeseed oil, rice bran oil, safflower oil, sesame oil, soybean oil, soya oil, sunflower oil, walnut oil, wheat germ oil, or a mixture thereof. Each of these oils is commercially available from a number of sources well recognized by those skilled in the art.

An oil is typically a mixture of various fatty acids. For example, rapeseed oil, obtained from the seeds of *Brassica Napus*, includes both omega-6 and omega-3 fatty acids in a ratio of about 2:1. As another example, linseed oil, obtained from the seeds of *Linum Usitatissimum*, includes about 7% palmitic acid, about 3.4-4.6% stearic acid, about 18.5-22.6% oleic acid, about 14.2-17% linoleic acid, and about 51.9-55.2% α-linolenic acid. In some instances, a pharmaceutical composition comprises an oil including at least two different fatty acids, at least three different fatty acids, at least four different fatty acids, at least five different fatty acids, or at least six different fatty acids.

A lipid useful in the pharmaceutical compositions may be a pharmaceutically acceptable glycerolipid. Glycerolipids are composed mainly of mono-, di-, and tri-substituted glycerols. One group of glycerolipids is the glycerides, where one, two, or all three hydroxyl groups of glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides. One group of glycerolipids is the glycerides, where one, two, or all three hydroxyl groups of glycerol have sugar residues attached via a glycosidic linkage.

In some instances, compositions may include one or more pharmaceutically acceptable stabilizing agents. A stabilizing agent reduces or eliminates formation of esters of a therapeutic compound that may result as a unwanted reaction with the particular solvent used. A stabilizing agent include, without limitation, water, a sacrificial acid comprising a fatty acid component and acetic acid, ethyl acetate, a sodium acetate/acetic acid (E262), a monoglyceride, an acetylated monoglyceride, a diglyceride, an acetylated monoglyceride, an acetylated diglyceride, a fatty acid, and a fatty acid salt.

In one embodiment, a pharmaceutically acceptable stabilizing agent may comprise a pharmaceutically acceptable emulsifying agent. An emulsifying agent (also known as an emulgent) is a substance that stabilizes an emulsion comprising a liquid dispersed phase and a liquid continuous phase by increasing its kinetic stability. Thus, in situations where the solvent and adjuvant used to make a pharmaceutical composition disclosed herein are normally immiscible, an emulsifying agent disclosed herein is used to create a homogenous and stable emulsion. An emulsifying agent includes, without limitation, a surfactant, a polysaccharide, a lectin, and a phospholipid.

An emulsifying agent may comprise a surfactant. As used hereon, the term "surfactant" refers to a natural or synthetic amphiphilic compound. A surfactant can be non-ionic, zwitterionic, or ionic. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), such as Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, such as BRIJ® 30, and BRIJ® 35; 2-dodecoxyethanol (LUBROL®-PX); polyoxyethylene octyl phenyl ether (TRITON® X-100); sodium dodecyl sulfate (SDS); 34(3-cholamidopropyl)dimethylammoniol-1-propanesulfonate (CHAPS); 3-[(3-cholamidopropyl)dimethylammoniol-2-hydroxy-1-propanesulfonate (CHAPSO); sucrose monolaurate; and sodium cholate. Other non-limiting examples of surfactant excipients can be found in, e.g., Ansel, supra, (1999); Gennaro, supra, (2000); Hardman, supra, (2001); and Rowe, supra, (2003), each of which is hereby incorporated by reference in its entirety.

An emulsifying agent may comprise a polysaccharide. Non-limiting examples of polysaccharides include guar gum, agar, alginate, calgene, a dextran (like dextran 1K, dextran 4K, dextran 40K, dextran 60K, and dextran 70K), dextrin, glycogen, inulin, starch, a starch derivative (like hydroxymethyl starch, hydroxyethyl starch, hydroxypropyl starch, hydroxybutyl starch, and hydroxypentyl starch), het-astarch, cellulose, FICOLL, methyl cellulose (MC), carboxymethyl cellulose (CMC), hydroxyethyl cellulose (HEC), hydroxypropyl cellulose (HPC), hydroxyethyl methyl cellulose (NEMC), hydroxypropyl methyl cellulose (HPMC); polyvinyl acetates (PVA); polyvinyl pyrrolidones (PVP), also known as povidones, having a K-value of less than or equal to 18, a K-value greater than 18 or less than or equal to 95, or a K-value greater than 95, like PVP 12 (KOLLIDON® 12), PVP 17 (KOLLIDON® 17), PVP 25 (KOLLIDON® 25), PVP 30 (KOLLIDON® 30), PVP 90 (KOLLIDON® 90); and polyethylene imines (PEI).

An emulsifying agent may comprise a lectin. Lectins are sugar-binding proteins that are highly specific for their sugar moieties. Lectins may be classified according to the sugar moiety that they bind to, and include, without limitation, mannose-binding lectins, galactose/N-acetylgalactosamine-binding lectins, N-acetylgluxosamine-binding lectins, N-acetylneuramine-binding lectins, N-acetylneuraminic acid-binding lectins, and fucose-binding lectins. Non-limiting examples of surfactants include concanavain A, lentil lectin, snowdrop lectin, Roin, peanut agglutinin, jacain, hairy vetch lectin, wheat germ agglutinin, elderberry lectin, Maackia anurensis leukoagglutinin, Maackia anurensis hemoagglutinin, Ulex europaeus agglutinin, and Aleuria aurantia lectin.

An emulsifying agent may comprise a phospholipid. The structure of the phospholipid generally comprises a hydrophobic tail and a hydrophilic head and is amphipathic in nature. Most phospholipids contain a diglyceride, a phosphate group, and a simple organic molecule such as choline;

one exception to this rule is sphingomyelin, which is derived from sphingosine instead of glycerol. Phospholipids include, without limitation, diacylglycerides and phosphosphingolipids. Non-limiting examples of diacylglycerides include a phosphatidic acid (phosphatidate) (PA), a phosphatidylethanolamine (cephalin) (PE), a phosphatidylcholine (lecithin) (PC), a phosphatidylserine (PS), and a phosphoinositide including phosphatidylinositol (PI), phosphatidylinositol phosphate (PIP), phosphatidylinositol bisphosphate (PIP2), and phosphatidylinositol triphosphate (PIP3). Non-limiting examples of phosphosphingolipids include a ceramide phosphorylcholine (sphingomyelin) (SPH), ceramide phosphorylethanolamine (sphingomyelin) (Cer-PE), and ceramide phosphorylglycerol.

The final concentration of a therapeutic compound in a pharmaceutical composition disclosed herein may vary over a wide range and generally may be characterized as a therapeutically effective amount. In some aspects, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

A pharmaceutical composition produced using the methods disclosed herein may be a liquid formulation or a solid or semi-solid formulation. A liquid formulation can be formed by using various lipids like oils of other fatty acids that remain as liquids in the temperature range desired. In an embodiment, a pharmaceutical composition disclosed herein is liquid at room temperature. In aspects of this embodiment, a pharmaceutical composition disclosed herein may be formulated to be a liquid at a temperature of, e.g., about 25° C. or higher, about 23° C. or higher, about 21° C. or higher, about 19° C. or higher, about 17° C. or higher, about 15° C. or higher, about 12° C. or higher, about 10° C. or higher, about 8° C. or higher, about 6° C. or higher, about 4° C. or higher, or about 0° C. or higher.

A solid or semi-solid formulation may take advantage of the different melting point temperatures of the various adjuvants like fatty acids. Formation of a solid or semi-solid dosage form can be by modifying the respective concentrations of the fatty acids comprising a pharmaceutical composition disclosed herein. For example, linolenic acid has a melting point temperature (Tm) of about −11° C., linoleic acid has a Tm of about −5° C., oleic acid has a Tm of about 16° C., palmitic acid has a Tm of about 61-62° C., and Stearic acid has a Tm of about 67-72° C. Increasing the proportion(s) of palmitic, stearic or oleic acid would increase the overall melting temperature of a composition, while, conversely, increasing the proportion(s) of linoleic and linolenic acid would decrease the melting temperature of a composition. Thus, by controlling the types and amounts of the adjuvant components added, a pharmaceutical composition disclosed herein can be made that is substantially solid or semi-solid at room temperature, but melts when it is ingested, and reaches body temperature. The resulting melted composition readily forms micelles which are absorbed by the intestine, assembled into chylomicrons, and ultimately absorbed by macrophages. The solid dosage form may be a powder, granule, tablet, capsule or suppository.

In some aspects, a pharmaceutical composition may be formulated as a chewing gum. The formulation of gum bases can vary substantially depending on the particular product to be prepared and on the desired masticatory and other sensory characteristics of the final product. By way of example, typical ranges of the gum base components include 5-80 wt. % elastomeric compounds, 5-80 wt. % natural and/or synthetic resins (elastomer plasticizers), 0-40 wt. % waxes, 5-35 wt. % softener other than waxes, 0-50 wt. % filler, and 0-5 wt. % of other ingredients such as antioxidants, colorants, and the like. The gum base may comprise about 5-95 wt. % of the total weight of the chewing gum, often from about 10-60 wt. % or from about 40-50 wt. %.

Often a buffer is used. Examples of buffers that may be used include tris buffers, amino acid buffers, carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, and mixtures thereof. Other examples of buffers include acetic acid, adipic acid, citric acid, fumaric acid, glucono-δ-lactone, gluconic acid, lactic acid, malic acid, maleic acid, tartaric acid, succinic acid, propionic acid, ascorbic acid, phosphoric acid, sodium orthophosphate, potassium orthophosphate, calcium orthophosphate, sodium diphosphate, potassium diphosphate, calcium diphosphate, pentasodium triphosphate, pentapotassium triphosphate, sodium polyphosphate, potassium polyphosphate, carbonic acid, sodium carbonate, sodium bicarbonate, potassium carbonate, calcium carbonate, magnesium carbonate, magnesium oxide, or any combination thereof.

The buffer may to some extent be microencapsulated or otherwise coated as granules with polymers and/or lipids being less soluble in saliva than is the one or more buffering agents. Such microencapsulation controls the dissolution rate whereby is extended the time frame of the buffering effect. The amount of buffer may range from 0 to about 15% and often ranges from about 0.5 to about 10% based on the total weight of the chewing gum.

Elastomers may be used to provide a rubbery, cohesive nature to the gum. Elastomers suitable for use in the gum base and gum may include natural or synthetic types. Elastomer plasticizers may be used to vary the firmness of the gum base. Their specificity on elastomer inter-molecular chain interaction (plasticizing) along with their varying softening points cause varying degrees of finished gum firmness and compatibility when used in base. This may provide more elastomeric chain exposure to the alkane chains of the waxes.

The elastomers employed in the gum base may vary depending upon various factors such as the type of gum base desired, the texture of gum formulation desired and the other components used in the formulation to make the final chewing gum product. The elastomer may be any water-insoluble polymer known in the art, and includes those gum polymers utilized for chewing gums and bubble gums. For example, polymers suitable for use in gum bases include, without limitation, natural substances (of vegetable origin) such as chicle gum, natural rubber, crown gum, nispero, rosidinha, jelutong, perillo, niger gutta, tunu, balata, gutta-percha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

Natural resins may be used according to the invention and may be natural rosin esters, often referred to as ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

Resins may be selected from terpene resins, such as those derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerized rosins, pentaerythritol esters of partially hydrogenated rosins, methyl esters of rosins, partially hydrogenated methyl esters of rosins or pentaerythritol esters of rosins and combinations thereof.

Other chewing gum ingredients may be selected from bulk sweeteners, flavors, dry-binders, tableting aids, anti-caking agents, emulsifiers, antioxidants, enhancers, absorption enhancers, buffers, high intensity sweeteners, softeners, colors, and combinations thereof. Non-limiting examples of emulsifiers include cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sobitan esters, diacetyl tartaric ester of monoglycerides, lactylated monoglycerides, and combinations thereof. The amount of emulsifiers often ranges from about 0.1% to about 25 wt. % based on the total weight of the chewing gum.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes. The compatibility of gum bases made using normal-alkanic waxes is less when compared to gum bases made with iso-alkanic waxes.

Petroleum wax (refined paraffin and microcrystalline wax) and paraffin wax are composed of mainly straight-chained normal-alkanes and branched iso-alkanes. The ratio of normal-alkanes to iso-alkanes varies.

The normal-alkanic waxes typically have carbon chain lengths >C-18 but the lengths are not predominantly longer than C-30. The branched and ring structures are located near the end of the chain for those waxes that are predominantly normal-alkanic. The viscosity of normal-alkanic waxes is <10 mm$^2$/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm$^2$/s (at 100° C.) and the combined number average molecular weight is >600 g/mole. Synthetic waxes are produced by means that are atypical for petroleum wax production and are thus not considered petroleum wax. The synthetic waxes may include waxes containing branched alkanes and copolymerized with monomers such as, but not limited to propylene, polyethylene, and Fischer Tropsch type waxes. Polyethylene wax is a synthetic wax containing alkane units of varying lengths having attached thereto ethylene monomers.

Waxes and fats are conventionally used for the adjustment of the texture and for softening of the chewing gum base when preparing chewing gum bases. Any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, such as completely or partially hydrogenated vegetable oils or completely or partially hydrogenated animal fats.

Antioxidants prolong shelf life and storage of gum base, finished gum or their respective components including fats and flavor oils. Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

A chewing gum may include other conventional components such as sweeteners, including bulk sweeteners, sugar sweeteners, sugar-substitute sweeteners, artificial sweeteners, high-intensity sweeteners, or a combination thereof. Bulk sweeteners may constitute from about 5 to about 95% by weight of the chewing gum, more typically about 20 to about 80% by weight, about 30 to 70%, or about 30 to 60% by weight of the gum.

Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination.

Sorbitol can be used as a non-sugar sweetener. Other useful non-sugar sweeteners include, but are not limited to, other sugar alcohols such as mannitol, xylitol, hydrogenated starch hydrolysates, maltitol, isomalt, erythritol, lactitol and the like, alone or in combination.

High intensity artificial sweetening agents can also be used alone or in combination with the above sweeteners. Non-limiting examples of high intensity sweeteners include sucralose, aspartame, salts of acesulfame, alitame, saccharin and its salts, cyclamic acid and its salts, glycyrrhizin, dihydrochalcones, thaumatin, monellin, sterioside and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the artificial sweetener will vary considerably and will depend on factors such as potency of the sweetener, rate of release, desired sweetness of the product, level and type of flavor used and cost considerations. The active level of artificial sweetener may vary from about 0.001 to about 8% by weight, and often ranges from about 0.02 to about 8% by weight. When carriers used for encapsulation are included, the usage level of the encapsulated sweetener will be proportionately higher. Combinations of sugar and/or non-sugar sweeteners may be used if desired.

A chewing gum and/or gum base may include one or more fillers/texturizers, such as magnesium and calcium carbonate, sodium sulfate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

A number of other well-known chewing gum components may be present, including but not limited to waxes, fats, softeners, fillers, flavors, anti-oxidants, emulsifiers, coloring agents, binding agents and acidulates. The chewing gum may be provided with an outer coating, such as a hard coating, soft coating, edible film-coating, or any combination thereof.

In some aspects, nicotine is compounded along with other components of the gum base such that nicotine is substantially uniformly contained in the gum base. Nicotine or a nicotine complex may be provided on an adsorbent such as finely divided silicic acid, amorphous silica, magnesium silicate, calcium silicate, kaolin, clays, crystalline aluminosilicates, macaloid bentonite, activated carbon, alumina, hydroxylapatite, microcrystalline cellulose, or any combination thereof. Nicotine may be encapsulated to provide a desired controlled or sustained release thereof. An example of a chewing gum that provides for sustained release of nicotine is described in U.S. 2007/0014887, the disclosure of which is hereby incorporated by reference. Alternatively, isomyosmine may be infused into an outer portion of a chewing gum than contains nicotine.

A similar release profile may be achieved via an oral dosage form such as a tablet, capsule, or the like. For example, a tablet may have a core layer containing nicotine to provide a sustained release thereof, and an outer layer containing isomyosmine to provide an immediate release thereof. Other combinations are possible. For example, one or both of the layers may contain both isomyosmine and nicotine so that the respective active component(s) is released in both an immediate- and a sustained release manner.

In other aspects, volatile delivery vehicles may be used for administering the active component(s) including isomyosmine, such as an inhaler or e-cigarette. In still other aspects, the active component(s) are administered transmucosally such as via a nasal spray, or transdermally such as via a transdermal patch.

A therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

Dosing can be single dosage or cumulative (serial dosing), and can be readily determined by one skilled in the art. For instance, treatment of a substance addiction may comprise a one-time administration of an effective dose of a pharmaceutical composition disclosed herein. Alternatively, treatment may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

The following example illustrates but does not limit the scope of the disclosure set forth above.

EXAMPLE 1

This example describes experiments for determining monoamine oxidase (MAO) inhibition for isomyosmine and other alkaloids. MAOs are enzymes located on the outer membrane of mitochondria and are involved in the catabolism of monoamine neurotransmitters. There are two well-characterized isoenzymes: MAO-A, which predominantly catabolizes serotonin and norepinephrine, and MAO-B, which preferentially catabolizes benzylamine and phenylethylamine. Dopamine and tyramine are metabolized by both isoforms.

To detect the activity of MAO, a luminescent method (MAO-Glo Assay kit, from Promega, Cat #V1401) was used. In this method, a MAO substrate (a derivative of beetle luciferin provided in the kit) is mixed with the compound to be tested (in this case, myosmine and control compounds). Then, the MAO enzymes (either A or B, purchased separately) are added to the mixture and incubated with the reaction for 1 hour at room temperature. The MAO enzymes, if not inhibited by the test compound, will convert the substrate into methyl ester luciferin. Finally, a luciferin detection reagent (provided by the kit) is added (20 minutes at room temperature) to stop the MAO reaction and convert methyl ester luciferin into D-luciferin. D-luciferin reacts with luciferase to produce a luminescent signal, which is directly proportional to the D-luciferin concentration and thus the MAO activity: the greater the amount of light produced the higher the activity of MAO. The luminescent signal is measured and recorded using a luminometer.

The following materials were obtained from Toronto Research Chemicals, North York, ON: isomyosmine, catalog #1821350; myosmine, catalog #M835000; anabasine, catalog #A637175; and nornicotine, catalog #N756995. Anatabine was obtained from Emerson Resources, Norristown, Pa.

As positive controls for the experiment, clorgyline (a well-characterized potent inhibitor of MAO-A) and deprenyl (a well-characterized potent inhibitor of MAO-B) were used.

Results for MAO-A Activity

Figure 1:
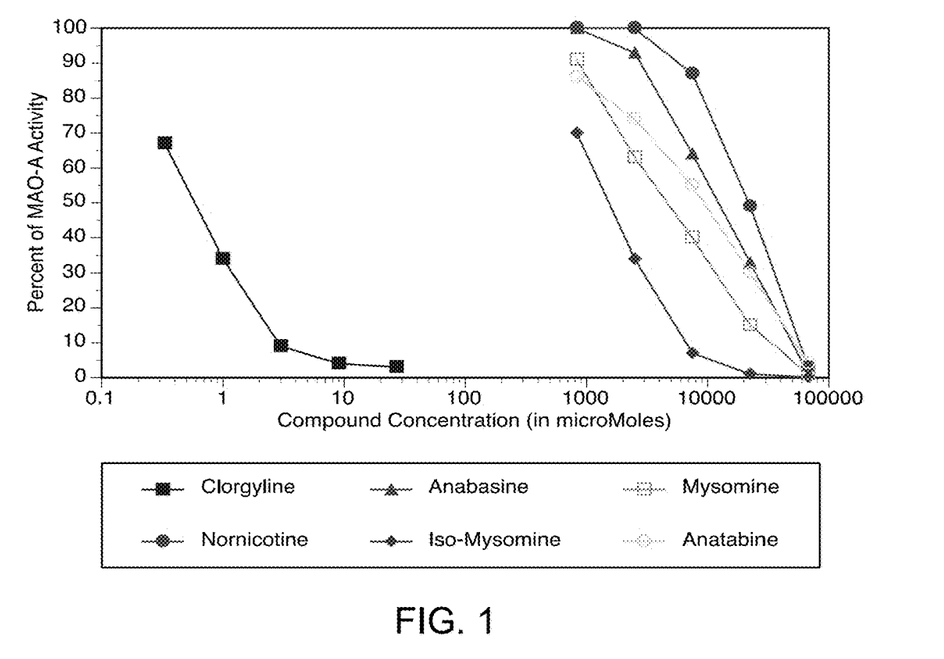
FIG. 1 is a graph showing the ability of isomyosmine, myosmine, anatabine, anabasine, and nornicotine to inhibit the enzymatic activity of MAO-A.

When the pure alkaloids isomyosmine, myosmine, anatabine, anabasine, and nornicotine were compared, isomyosmine was the most potent of the five in inhibiting the enzymatic activity of MAO-A (FIG. 1). The way to read this line graph is the following: a 100% activity means that the test compound has no effect on the enzyme; a 0% activity means that the test compound completely kills the enzyme. The more the curve is shifted to the left, the greater the inhibition the test compound exerts on the enzyme. As can be seen in FIG. 1, the curve for isomyosmine is more shifted to the left among the five alkaloids tested. A 2 mM concentration (2,000 micromolar) gives an inhibition of about 50%. The curve for clorgyline, the positive control for the experiment, is greatly shifted leftward.

Results for MAO-B Activity

Figure 2:
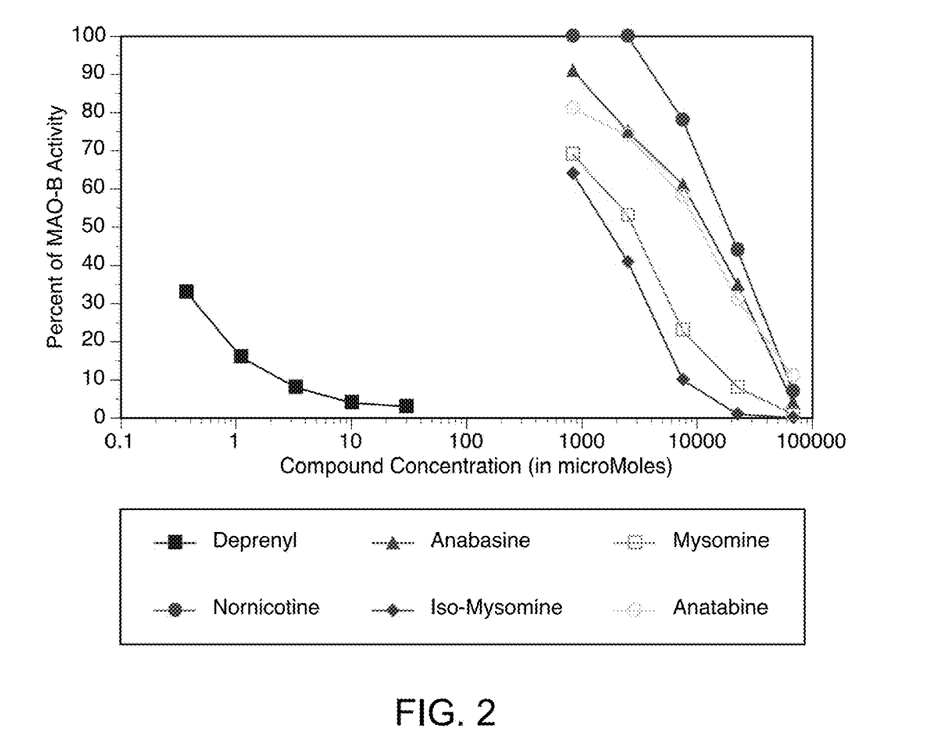
FIG. 2 is a graph showing the ability of isomyosmine, myosmine, anatabine, anabasine, and nornicotine to inhibit the activity of MAO-B.

Similar results were obtained when testing the five pure alkaloids isomyosmine, myosmine, anatabine, anabasine, and nornicotine for the inhibition of MAO-B. Isomyosmine was the most potent among the five alkaloids tested at inhibiting the activity of MAO-B, followed by myosmine (FIG. 2).

EXAMPLE 2

Figure 3:
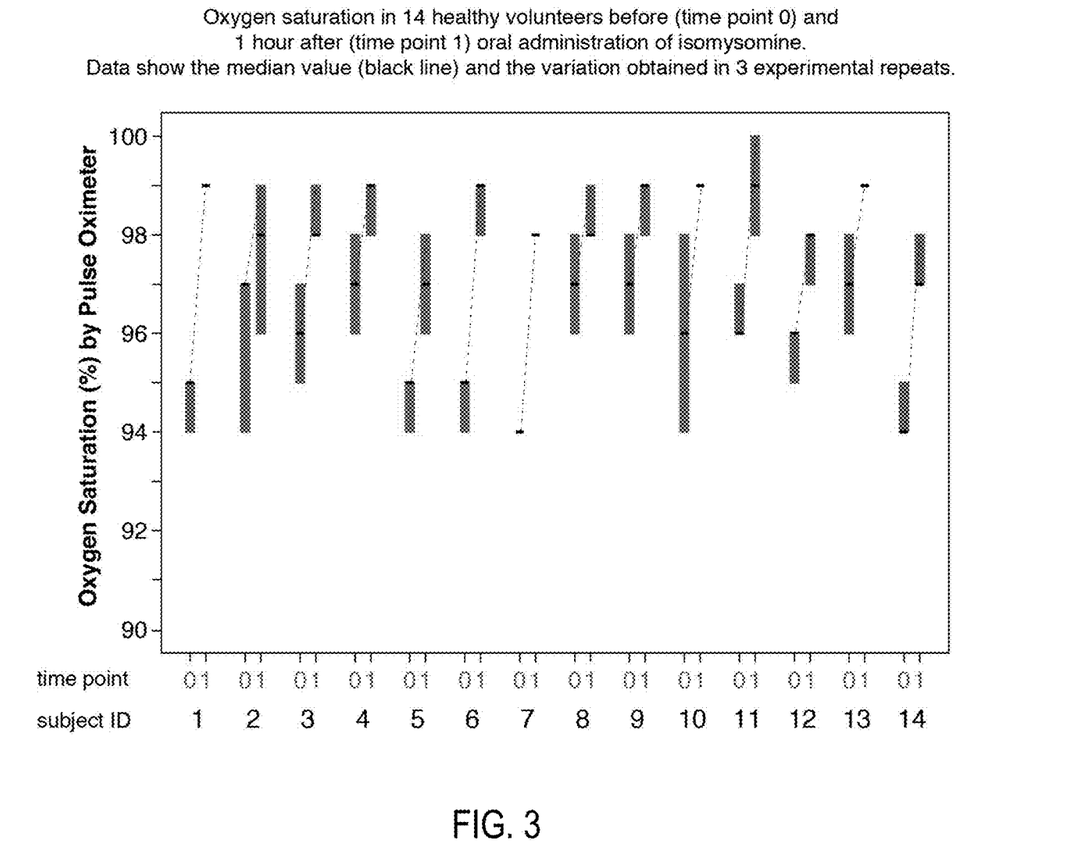
FIG. 3 is a graph showing oxygen saturation (%) in individuals before and one hour after oral administration of isomyosmine.

This example shows that isomyosmine is effective to increase oxygen saturation (%) levels. As shown in FIG. 3, oxygen saturation (%) was found to dramatically increase in fourteen individuals when measured one hour after oral administration of isomyosmine at a dose of 100-300 mg depending on body weight. Increasing oxygen saturation levels is believed to make isomyosmine particularly effective for treating substance addictions, including tobacco/nicotine addictions, as well as addictions to heroin, cocaine, opioids, methadone, d-methamphetamine, barbiturates, alcohol, benzodiazepines, amphetamines, or buprenorphine. For example, substances such as cocaine are known to cause blood vessels to constrict, resulting in increased heartrate and blood pressure and increased stress on the heart's ability to circulate blood and oxygen through the body. Increasing oxygen saturation levels may, among other things, counteract these types of effects associated with substance abuse by increasing blood oxygen levels, aiding in the treatment of the underlying addiction.

While the invention has been described with respect to specific examples, those skilled in the art will appreciate that there are numerous variations and permutations of the above described systems and techniques that fall within the spirit and scope of the invention as set forth in the appended claims.

What is claimed is:

1. A method of treating a cocaine addiction comprising administering to an individual in need thereof a pharmaceutical composition comprising a therapeutically effective amount of isomyosmine or a pharmaceutically acceptable salt thereof and a pharmaceutically acceptable vehicle therefor.

2. The method of claim 1, wherein the pharmaceutical composition is administered via a capsule, tablet, or lozenge.

3. The method of claim 1, wherein the pharmaceutical composition contains isomyosmine or a pharmaceutically acceptable salt thereof in an amount from about 5 mg to about 1,500 mg.

4. The method of claim 1, wherein the pharmaceutical composition contains isomyosmine or a pharmaceutically acceptable salt thereof in an amount from about 10 mg to about 1,200 mg.

5. The method of claim 1, wherein the pharmaceutical composition contains isomyosmine or a pharmaceutically acceptable salt thereof in an amount from about 50 mg to about 1,000 mg.

6. The method of claim 1, wherein the pharmaceutical composition contains isomyosmine or a pharmaceutically acceptable salt thereof in an amount from about 100 mg to about 850 mg.

7. The method of claim 1, wherein the pharmaceutical composition further comprises a second therapeutic agent.

8. The method of claim 7, wherein the second therapeutic agent comprises an anti-inflammatory compound.

9. The method of claim 7, wherein the pharmaceutical composition contains the second therapeutic agent in an amount from about 5 mg to about 1,500 mg.

10. The method of claim 7, wherein the pharmaceutical composition contains the second therapeutic agent in an amount from about 10 mg to about 1,200 mg.

* * * * *